US009180160B2

(12) United States Patent
Lambris et al.

(10) Patent No.: US 9,180,160 B2
(45) Date of Patent: Nov. 10, 2015

(54) COMPLEMENT INHIBITORS FOR TREATMENT OF INJURY FROM INTRACEREBRAL HEMORRHAGE

(75) Inventors: John D. Lambris, Philadelphia, PA (US); E. Sander Connolly, Jr., New York, NY (US)

(73) Assignees: The Trustees of the University of Pennsylvania, Philadelphia, PA (US); The Trustees of Columbia University, New York, NY (US)

( * ) Notice: Subject to any disclaimer, the term of this patent is extended or adjusted under 35 U.S.C. 154(b) by 338 days.

(21) Appl. No.: 13/059,482

(22) PCT Filed: Aug. 19, 2009

(86) PCT No.: PCT/US2009/054308
§ 371 (c)(1),
(2), (4) Date: Jun. 27, 2011

(87) PCT Pub. No.: WO2010/022149
PCT Pub. Date: Feb. 25, 2010

(65) Prior Publication Data
US 2011/0256136 A1   Oct. 20, 2011

Related U.S. Application Data

(60) Provisional application No. 61/090,341, filed on Aug. 20, 2008.

(51) Int. Cl.
*A61K 38/08* (2006.01)
*A61K 45/06* (2006.01)
*C07K 16/28* (2006.01)
*A61K 38/12* (2006.01)

(52) U.S. Cl.
CPC ............ *A61K 38/08* (2013.01); *A61K 38/12* (2013.01); *A61K 45/06* (2013.01); *C07K 16/2896* (2013.01)

(58) Field of Classification Search
None
See application file for complete search history.

(56) References Cited

U.S. PATENT DOCUMENTS

| | | | |
|---|---|---|---|
| 6,180,370 | B1 | 1/2001 | Queen et al. |
| 6,319,897 | B1 | 11/2001 | Lambris et al. |
| 2003/0224490 | A1 | 12/2003 | Dessain et al. |
| 2006/0217530 | A1 | 9/2006 | Maxwell et al. |
| 2007/0093443 | A1* | 4/2007 | Madison et al. .......... 514/44 |
| 2008/0113904 | A1* | 5/2008 | Woodruff et al. .......... 514/9 |
| 2008/0233113 | A1* | 9/2008 | Bansal ................. 424/133.1 |
| 2010/0166862 | A1* | 7/2010 | Francois et al. ............ 424/484 |

FOREIGN PATENT DOCUMENTS

| | | |
|---|---|---|
| WO | WO 99/13899 A1 | 3/1999 |
| WO | WO 2004/026328 A1 | 4/2004 |
| WO | WO 2010/022149 A1 | 2/2010 |

OTHER PUBLICATIONS

Rynkowski et al. "C3a receptor antagonist attenuates brain injury after intracerebral hemorrhage" J.C.B.F.M., 29, 2009, 98-107.*
Calbiochem product guide, 559410 SB290157, 2012, pp. 1-2.*
Arumugam et al., "A small molecule C5a receptor antagonist protects kidney from ischemia/reperfusion injury", Kidney Int., vol. 63, pp. 134-142 (2003).
Atkinson et al., "Complement-Dependent P-Selectin Expression and Injury following Ischemic Stroke", J. Immunol. vol. 77. pp. 134-142 (2003).
Bao et al., "C5a promotes development of experimental lupus nephritis which can be blocked with a specific receptor . . . ", Eur. J. Immunol., vol. 35, pp. 2496-2506 (2005).
Bird et al., "Single-chain antigen-binding proteins", Science, vol. 242, pp. 423-426 (1988).
Burton et al., "Human antibodies from combinatorial libraries", Adv. Immunol., vol. 57, pp. 191-280 (1994).
Costa et al., "Role of complement component C5 in cerebral ischemia/reperfusion injury", Brain Res., vol. 1100, pp. 142-151 (2006).
De Simoni et al., "Neuroprotection by complement (C1) inhibitor in mouse transient brain ischemia", J. Cereb. Blood Flow Metab., vol. 23, pp. 232-239 (2003).
De Vries et al., "Complement Factor C5a Mediates Renal Ischemia-Reperfusion Injury Independent from Neutrophils", J. Immunol., vol. 170, pp. 3883-3889 (2003).
Ducruet et al., "C3a receptor modulation of granulocyte infiltration after murine focal cerebral ischemia is . . . ", J. Cereb. Blood Flow Metab., vol. 28, pp. 1048-1058 (2008).
Elsner et al., "C3a Activates the Respiratory Burst in Human Polymorphonuclear Neutrophilic Leukocytes Via Pertussis Toxin . . . ", Blood, vol. 83, pp. 3324-3331 (1994).
Figueroa et al,. "The administration of cobra venom factor reduces post-ischemic cerebral injury in adult and neonatal rats", Neurosci. Lett., vol. 380, pp. 48-53 (2005).
Fleming et al., "C5a causes limited, polymorphonuclear cell-independent, mesenteric ischemia/reperfusion-induced injury", Clin. Immunol., vol. 108, pp. 263-273 (2003).
Gu et al., "Construction and expression of mouse-human chimeric antibody SZ-51 specific for activated platelet P-selectin", Thromb. Hema., vol. 77, pp. 755-759 (1997).
Hammel et al., "Characterization of Ehp, a secreted complement inhibitory protein from *Staphylococcus aureus*", J. Biol. Chem., vol. 282, pp. 30051-30061 (2007).

(Continued)

*Primary Examiner* — Daniel E Kolker
*Assistant Examiner* — James Rogers
(74) *Attorney, Agent, or Firm* — Potter Anderson and Corroon LLP

(57) ABSTRACT

Methods for treating or ameliorating the damage resulting from intracerebral hemorrhage are disclosed. The methods involve administration of a complement inhibitor to inhibit C3a or C5a formation or activity in the affected tissue. Pharmaceutical compositions suitable for use in the methods of the invention are also provided.

10 Claims, 10 Drawing Sheets

(56) References Cited

OTHER PUBLICATIONS

Heller et al., "Selection of a C5a Receptor Antagonist from Phage Libraries Attenuating the Inflammatory Response in Immune . . . ", J. Immunol., vol. 163, pp. 985-994 (1999).

Hua et al., "Complement activation in the brain after experimental intracerebral hemorrhage", J. Neurosurg., vol. 92, pp. 1016-1022 (2000).

Huston et al., "Protein engineering of antibody binding sites: recovery of specific activity in an anti- . . . ", Proc. Natl. Acad. Sci. USA, vol. 85, pp. 5879-5883 (1988).

Lee et al., "Identification and Characterization of the C3 Binding Domain of the *Staphylococcus aureus* Extra . . . ", J. Biol. Chem., vol. 279, pp. 50710-50716 (2004).

Mocco et al., "Complement Component C3 Mediates Inflammatory Injury Following Focal Cerebral Ischemia", Circ. Res., vol. 99, pp. 209-217 (2006).

Morikis et al., "Design, Structure, Function and Application of Compstatin" in Bioactive Peptides . . . , IOS Press, Amsterdam NL, pp. 235-246 (1999).

Nakamura et al., "Intracerebral hemorrhage in mice: model characterization and application for genetically ", J. Cereb. Blood Flow Metab., vol. 24, pp. 487-494 (2004).

Pasinetti et al., "Hereditary deficiencies in complement C5 are associated with intensified neurodegenerative responses . . . " Neurobiol. Dis., vol. 3, pp. 197-204 (1996).

Proctor et al., "Transdermal pharmacology of small molecule cyclic C5a antagonists", Adv. Exp. Med. Biol., vol. 586, pp. 329-345 (2006).

Rynkowski et al., "A mouse model of intracerebral hemorrhage using autologous blood infusion", Nat. Protoc., vol. 3, pp. 122-128 (2008).

Soruri et al., "IL-4 down-regulates anaphylatoxin receptors in monocytes and dendritic cells and impairs anaphylatoxin-induced . . . ", J. Immunol., vol. 170, pp. 3306-3314 (2003).

Stahel et al., "The role of the complement system in traumatic brain injury", Brain Res. Rev., vol. 27, pp. 243-256 (1998).

Tuszynski et al., "Thrombospondin promotes platelet aggregation", Blood, vol. 72, pp. 109-115 (1988).

Vasthare et al., "Complement depletion improves neurological function in cerebral ischemia", Brain Res. Bull., vol. 45, pp. 413-419 (1998).

Wada et al., "Inhibition of complement C5 reduces local and remote organ injury after intestinal ischemia/reperfusion in . . . ", Gastroenterology, vol. 120, pp. 126-133 (2001).

Woodruff, et al., "Therapeutic activity of C5a receptor antagonists in a rat model of neurodegeneration", FASEB J., vol. 20, pp. 1407-1417 (2006).

Wright et al., "Genetically engineered antibodies: progress and prospects", Crit. Rev. Immunol., vol. 12, pp. 125-168 (1992).

Xi et al., "Systemic complement depletion diminishes perihematomal brain edema in rats", Stroke, vol. 32, pp. 162-167 (2001).

Xi et al., "Brain edema after intracerebral hemorrhage: the effects of systemic complement depletion", Acta Neurachir. Suppl., vol. 81, pp. 253-256 (2002).

Yang et al., "The role of complement C3 in intracerebral hemorrhage-induced brain injury", J. Cereb. Blood Flow Metab., vol. 26, pp. 1490-1495 (2006).

International Search Report in PCT/US2009/054308, mailed Jan. 26, 2010.

\* cited by examiner

SEQUENCE LISTING

<160> NUMBER OF SEQ ID NOS: 3

<210> SEQ ID NO 1
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: DISULFID
<222> LOCATION: (2)..(12)

<400> SEQUENCE: 1

Ile Cys Val Val Gln Asp Trp Gly His His Arg Cys Thr
1               5                   10

<210> SEQ ID NO 2
<211> LENGTH: 16
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: Xaa is Gly or is missing
<220> FEATURE:
<221> NAME/KEY: VARIANT
<222> LOCATION: (2)..(2)
<223> OTHER INFORMATION: Xaa is Ile, Val, Leu, Ac-Ile, Ac-Val or Ac-Leu
<220> FEATURE:
<221> NAME/KEY: DISULFID
<222> LOCATION: (3)..(13)
<220> FEATURE:
<221> NAME/KEY: VARIANT
<222> LOCATION: (5)..(5)
<223> OTHER INFORMATION: Xaa is Trp or an analog of Trp
<220> FEATURE:
<221> NAME/KEY: VARIANT
<222> LOCATION: (10)..(10)
<223> OTHER INFORMATION: Xaa is His, Ala, Phe or Trp
<220> FEATURE:
<221> NAME/KEY: VARIANT
<222> LOCATION: (14)..(14)
<223> OTHER INFORMATION: Xaa is L-Thr, D-Thr, Ile, Val or Gly
<220> FEATURE:
<221> NAME/KEY: VARIANT
<222> LOCATION: (15)..(15)
<223> OTHER INFORMATION: Xaa is Asn or Ala, or is missing
<220> FEATURE:
<221> NAME/KEY: VARIANT
<222> LOCATION: (16)..(16)
<223> OTHER INFORMATION: Xaa is Asn, or is missing

<400> SEQUENCE: 2

Xaa Xaa Cys Val Xaa Gln Asp Trp Gly Xaa His Arg Cys Xaa Xaa Xaa
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: Xaa is Gly or is missing
<220> FEATURE:
<221> NAME/KEY: VARIANT
<222> LOCATION: (2)..(2)
<223> OTHER INFORMATION: Xaa is Ile, Val, Leu, Ac-Ile, Ac-Val or Ac-Leu
<220> FEATURE:
<221> NAME/KEY: DISULFID

```
<222> LOCATION: (3)..(13)
<220> FEATURE:
<221> NAME/KEY: VARIANT
<222> LOCATION: (5)..(5)
<223> OTHER INFORMATION: Xaa is Trp or an analog of Trp
<220> FEATURE:
<221> NAME/KEY: VARIANT
<222> LOCATION: (8)..(8)
<223> OTHER INFORMATION: Xaa is Trp or an analog of Trp
<220> FEATURE:
<221> NAME/KEY: VARIANT
<222> LOCATION: (10)..(10)
<223> OTHER INFORMATION: Xaa is His, Ala, Phe or Trp
<220> FEATURE:
<221> NAME/KEY: VARIANT
<222> LOCATION: (14)..(14)
<223> OTHER INFORMATION: Xaa is L-Thr, D-Thr, Ile, Val or Gly
<220> FEATURE:
<221> NAME/KEY: VARIANT
<222> LOCATION: (15)..(15)
<223> OTHER INFORMATION: Xaa is Asn or Ala, or is missing
<220> FEATURE:
<221> NAME/KEY: VARIANT
<222> LOCATION: (16)..(16)
<223> OTHER INFORMATION: Xaa is Asn, or is missing

<400> SEQUENCE: 3

Xaa Xaa Cys Val Xaa Gln Asp Xaa Gly Xaa His Arg Cys Xaa Xaa Xaa
1               5                   10                  15
```

COMPLEMENT INHIBITORS FOR TREATMENT OF INJURY FROM INTRACEREBRAL HEMORRHAGE

This invention was made with government support under Grant Nos. NS 40409 and GM-62134 awarded by the National Institutes of Health. The government has certain rights in the invention.

FIELD OF THE INVENTION

This invention relates to the field neurological injury and treatment. Methods for treating injury resulting from intracerebral hemorrhage are provided. The methods involve administration of a complement inhibitor to inhibit C3a receptor and/or C5a receptor signaling in affected tissue.

BACKGROUND OF THE INVENTION

Various publications, including patents, published applications, technical articles and scholarly articles are cited throughout the specification. Each of these cited publications is incorporated by reference herein, in its entirety. Full citations for publications not cited fully within the specification are set forth at the end of the specification.

Hemorrhagic stroke accounts for approximately 15% of all strokes but is associated with a disproportionate degree of morbidity. Studies have indicated that inflammatory processes and complement activation in particular may be involved in exacerbating brain injury after the hemorrhagic event (Hua Y, et al., 2000, *J Neurosurg.* 92: 1016-1022). Early attempts at complement inhibition using cobra venom factor, C1-esterase inhibitor, and soluble complement receptor-1 revealed reduced edema formation in hemorrhagic models (Xi G, et al., 2001, *Stroke* 32: 162-167; Xi G, et al., 2002, *Acta Neurochir Suppl.* 81: 253-256) and decreased infarct volumes in animal stroke models (Figueroa E, et al., 2005, *Neurosci Lett.* 380: 48-53; De Simoni M G, et al., 2003, *J Cereb Blood Flow Metab.* 23: 232-239; Vasthare U S, et al., 1998, *Brain Res Bull.* 45: 413-419). However, the lack of specificity of these agents left it unclear as to which complement components are most relevant in the pathogenesis of cerebral injury.

C3a and C5a, collectively known as the anaphylotoxins, induce a wide variety of cellular responses, including chemotaxis, degranulation, oxidative bursts, and disruption of the blood brain barrier (Elsner J, et al., 1994, *Blood* 83: 3324-3331; Soruri A, et al. 2003, *J. Immunol.* 170: 3306-3314; Stahel P F, et al., 1998, *Brain Res Rev.* 27: 243-256). Recent studies have revealed that functional inhibitors as well as genetic knockouts of C3 were protective against and ICH-induced edema (Yang S, et al., 2006, *J Cereb Blood Flow Metab.* 26: 1490-1495) and cerebral ischemic/reperfusion injury (Motto J, et al., 2006, *Circ Res.* 99: 209217; Ducruet A F, et al., 2008, *J Cereb Blood Flow Metab.* 28: 1048-1058; Atkinson C, et al., 2006, *J. Immunol.* 177: 7266-7274).

However, attempts to inhibit C5 have met with conflicting results. Genetic knockouts of C5 have shown increased vulnerability to ICH (Nakamura T, et al., 2004, *J Cereb Blood Flow Metab.* 24: 487-494), ischemic stroke (Yang et al., 2006, supra), and excito-toxic injury (Pasinetti G M, et al., 1996, *Neurobiol Dis.* 3: 197-204). In contrast, functional inhibition of C5 and the C5a receptor have shown neuro-protection against ischemia-reperfusion injury in MCAO models (Costa C, et al., 2006, *Brain Res.* 1100: 142-151) as well as visceral (Fleming S D, et al., 2003, *Clin Immunol.* 108: 263-273; Wada K, et al., 2001, *Gastroenterology* 120: 126-133) and renal models (de Vries B, et al., 2003, *J Immunol.* 170: 3883-3889; Bao L, et al., 2005, *Eur J. Immunol.* 35: 2496-2506; Heller T, et al., 1999, *J Immunol.* 163: 985-994; Arumugam T V, et al., 2003, *Kidney Int.* 63: 134-142).

Intracerebral hemorrhage (ICH) is a devastating disease process, which has a 30-50% mortality rate that has not improved over the past two decades. Currently available therapies are limited to supportive medical therapy and surgery for only a select group of patients. Thus, there is a need in the art to identify and develop new therapies for the treatment of ICH. This invention addressed those needs.

SUMMARY OF THE INVENTION

One aspect of the invention features a method for treating or preventing injury resulting from intracerebral hemorrhage in an individual. The method comprises administering a therapeutically effective amount of a complement inhibitor to the individual, wherein the complement inhibitor reduces or prevents C3a or C5a formation or activity, thereby treating or preventing the injury resulting from intracerebral hemorrhage. The complement inhibitor can comprise one or more of a C5a inhibitor, a C5aR inhibitor, a C3 inhibitor, a C3aR inhibitor, a factor D inhibitor, a factor B inhibitor, a C4 inhibitor, a C1q inhibitor, or any combination thereof. In certain embodiments, the complement inhibitor is a C5a inhibitor or a C5aR inhibitor, including but not limited to acetyl-Phe-[Orn-Pro-D-cyclohexylalanine-Trp-Arg] (PMX-53), PMX-53 analogs, neutrazumab, TNX-558, eculizumab, pexelizumab or ARC1905, or any combination thereof. In other embodiments, the complement inhibitor is a C3 inhibitor, including but not limited to compstatin, a compstatin analog, a compstatin peptidomimetic, a compstatin derivative, or any combinations thereof. In other embodiments, the complement inhibitor is a C4 inhibitor. A combination of complement inhibitors forms another embodiment.

The complement inhibitor may administered at or targeted to affected tissue, or it may be administered systemically. The complement inhibitor can be administered together or concurrently with, or sequentially before or after, at least one other agent for treatment of injury resulting from intracerebral hemorrhage.

According to another aspect of the invention, pharmaceutical compositions useful for practicing the methods of the invention are also provided. These compositions comprise a pharmaceutically acceptable carrier and an amount of one or more complement inhibitors effective to treat or prevent injury resulting from intracerebral hemorrhage. The complement inhibitor can comprise one or more of a C5a inhibitor, a C5aR inhibitor, a C3 inhibitor, a C3aR inhibitor, a factor D inhibitor, a factor B inhibitor, a C4 inhibitor, a C1q inhibitor, or any combination thereof. In certain embodiments, the complement inhibitor is a C5a inhibitor or a C5aR inhibitor, including but not limited to acetyl-Phe-[Orn-Pro-D-cyclohexylalanine-Trp-Arg] (PMX-53), PMX-53 analogs, neutrazumab, TNX-558, eculizumab, pexelizumab or ARC1905, or any combination thereof. In other embodiments, the complement inhibitor is a C3 inhibitor, including but not limited to compstatin, a compstatin analog, a compstatin peptidomimetic, a compstatin derivative, or any combinations thereof. In other embodiments, the complement inhibitor is a C4 inhibitor. A combination of complement inhibitors forms another embodiment. Yet another embodiment features a pharmaceutical composition comprising one or more complement inhibitors and one or more additional agents useful for the treatment or prevention of injury resulting from intracerebral hemorrhage.

Other features and advantages of the invention will be understood by reference to the drawings, detailed description and examples that follow.

DETAILED DESCRIPTION OF ILLUSTRATIVE EMBODIMENTS

Figure 1:
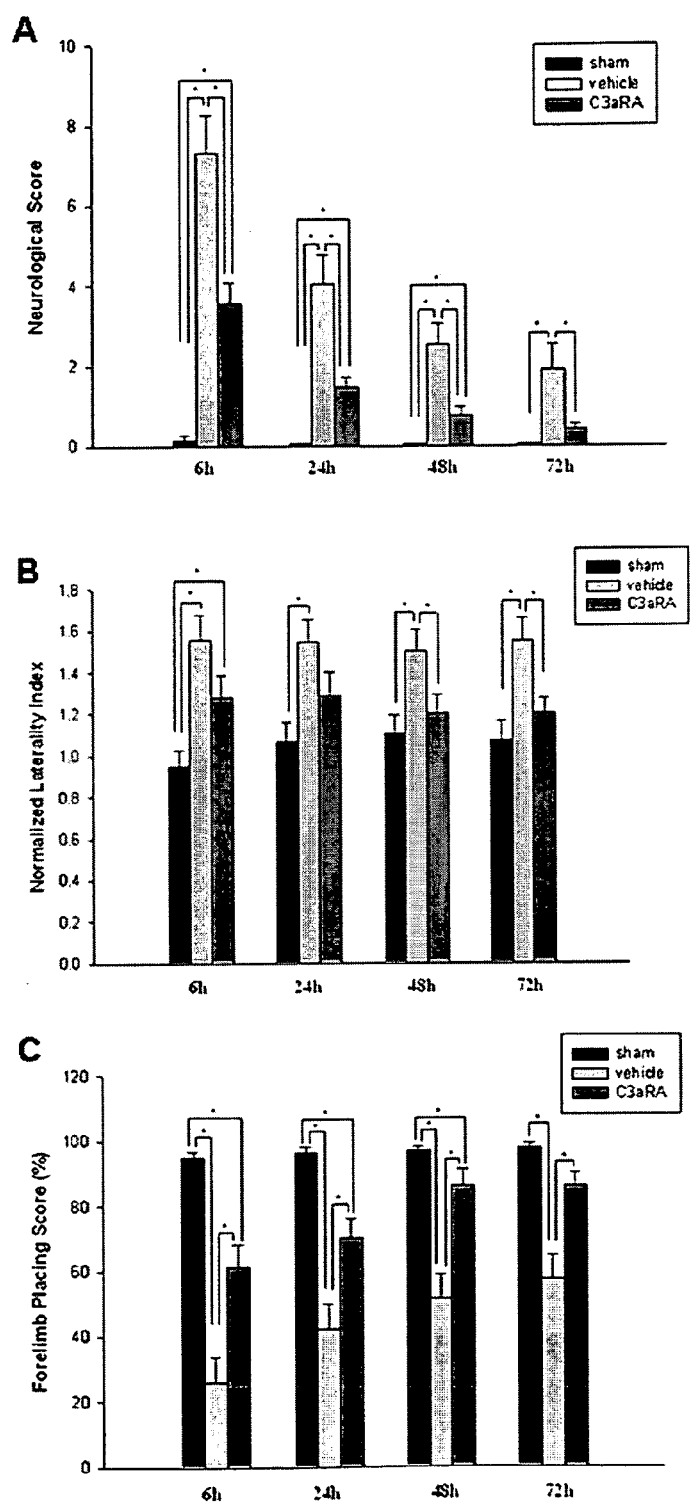
FIG. 1. Total neurological score (A), corner test performance expressed by the normalized laterality index (B) and forelimb placing capacity in the impaired limb (C) in sham (n=13), vehicle-treated (n=24) and C3aRA-treated (n=24) groups at 6, 24, 48 and 72 hours after intrastriatal infusion of 30 μL autologous blood. Values are expressed as mean±SEM. An * signifies P<0.05.

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

Standard techniques are used for nucleic acid and peptide synthesis. The techniques and procedures are generally performed according to conventional methods in the art and various general references (e.g., Sambrook and Russell, 2001, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document.

The nomenclature used herein and the laboratory procedures used in analytical chemistry and organic syntheses described below are those well known and commonly employed in the art. Standard techniques or modifications thereof, are used for chemical syntheses and chemical analyses.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. The antibodies useful in the present invention may exist in a variety of forms including, for example, polyclonal antibodies, monoclonal antibodies, intracellular antibodies ("intrabodies"), Fv, Fab and F(ab)$_2$, as well as single chain antibodies (scFv), camelid antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

As used herein, a "complement inhibitor" is a molecule that prevents or reduces activation and/or propagation of the complement cascade that results in the formation of C5a or signaling through the C5a receptor. A complement inhibitor can operate on one or more of the complement pathways, i.e., classical, alternative or lectin pathway.

As used herein, a "C3 inhibitor" is a molecule or substance that prevents or reduces the cleavage of C3 into C3a and C3b.

As used herein, a "C5a inhibitor" is a molecule or substance that prevents or reduces the activity of C5a.

As used herein, a "C5aR inhibitor" is a molecule or substance that prevents or reduces the binding of C5a to the C5a receptor.

As used herein, a "C3aR inhibitor" is a molecule or substance that prevents or reduces binding of C3a to the C3a receptor.

As used herein, a "factor D inhibitor" is a molecule or substance that prevents or reduces the activity of Factor D.

As used herein, a "factor B inhibitor" is a molecule or substance that prevents or reduces the activity of factor B.

As used herein, a "C4 inhibitor" is a molecule or substance that prevents or reduces the cleavage of C4 into C4b and C4a.

As used herein, a "C1q inhibitor" is a molecule or substance that prevents or reduces C1q binding to antibody-antigen complexes, virions, infected cells, or other molecules to which C1q binds to initiate complement activation.

Any of the inhibitors described herein may comprise antibodies or antibody fragments, as would be understood by the person of skill in the art.

"Treating" refers to any indicia of success in the treatment or amelioration of the disease or condition. Treating can include, for example, reducing or alleviating the severity of one or more symptoms of the disease or condition, or it can include reducing the frequency with which symptoms of a disease, defect, disorder, or adverse condition, and the like, are experienced by a patient.

"Preventing" refers to the partial or complete prevention of the disease or condition in an individual or in a population. The term "prevention" does not establish a requirement for complete prevention of a disease in the entirety of the treated population.

The term "treat or prevent" is sometimes used herein to refer to a method that results in some level of treatment or amelioration of the disease or condition, and contemplates a range of results directed to that end, including but not restricted to prevention of the condition entirely.

A "prophylactic" treatment is a treatment administered to a subject who does not exhibit signs of a disease or condition, or exhibits only early signs of the disease or condition, for the purpose of decreasing the risk of developing pathology associated with the disease or condition. This term may be used interchangeably with the term "preventing," again with the understanding that such prophylactic treatment or "prevention" does not establish a requirement for complete prevention of a disease or condition in the entirety of the treated population.

As used herein, an "effective amount," or a "therapeutically effective amount" is the amount of a composition sufficient to provide a beneficial effect to the individual to whom the composition is administered.

The term "individual" or "patient" refers to a human or any animal. Thus, the methods and compositions of the invention may be used in pharmaceutical and veterinary applications.

It is understood that any and all whole or partial integers between any ranges set forth herein are included herein.

Description

The complement cascade is integral in initiating and modifying the inflammatory process through its influence on neutrophil chemotaxis, upregulation of vascular permeability, and subsequent edema formation. The development of clinically useful therapies has been hindered, however, by insufficient understanding of which complement subcomponents contribute to post-hemorrhagic injury.

The present invention springs in part from the inventors' demonstration that both C3a and C5a signaling are involved in post-hemorrhagic neurological injury and that pharmaceutical blockade of Ca3 and/or C5a signaling, or dual blockade of both, results in a significant neuro-protective effect. In particular, the inventors have shown that ICH-induced brain edema formation and neurological deficits are reduced in animals treated with a C3a receptor antagonist (C3aRA) both prior to, and following induction of ICH, compared to vehicle-treated animals. Additionally, granulocyte infiltration was shown to be significantly less in subjects pre-treated with the C3aRA. The inventors also demonstrated a beneficial effect of treatment with a C5a receptor antagonist (CSaRA) and with a combination therapy. With respect to the latter, it was shown that combined C3aRA/C5aRA therapy given six hours after induced intracerebral hemorrhage led to particularly improved neurofunctional outcome while reducing inflammatory cell infiltration and brain edema.

Accordingly, one aspect of the present invention features a method for treating or preventing injury resulting from intracerebral hemorrhage in an individual. The method comprises administering a therapeutically effective amount of a complement inhibitor to the individual, wherein the complement inhibitor reduces or prevents C3a or C5a formation or activity, thereby treating or preventing the injury resulting from intracerebral hemorrhage.

As mentioned above, a "complement inhibitor" is a molecule that prevents or reduces activation and/or propagation of the complement cascade that results in (1) the formation of C3a or signaling through the C3a receptor, also referred to herein as "C3a activity," or (2) the formation of C5a or signaling through the C5a receptor, also referred to herein as "C5a activity". A complement inhibitor can operate on one or more of the complement pathways, i.e., classical, alternative or lectin pathway.

Any inhibitor of C5a formation or activity may be used in the method of the invention. Inhibition of C5a formation or activity may be accomplished in a variety of ways. For instance, C5a activity may be inhibited directly by preventing or significantly reducing the binding of C5a to its receptor, C5aR. A number of C5aR inhibitors are known in the art. Acetyl-Phe-[Orn-Pro-D-cyclohexylalanine-Trp-Arg] (AcF[OPdChaWR]; PMX-53; Peptech) is a small cyclic hexapeptide that is a C5aR antagonist and is exemplified herein. Analogs of PMX-53 (e.g., PMX-201 and PMX-205) that also function as C5aR antagonists are also available (see for instance Proctor et al., 2006, *Adv Exp Med. Biol.* 586:329-45 and U.S. Pat. Pub. No. 20060217530). Neutrazumab (G2 Therapies) binds to C5aR, thereby inhibiting binding of C5a to C5aR. Neutrazumab (G2 Therapies) binds to extracellular loops of C5aR and thereby inhibits the binding of C5a to C5aR. TNX-558 (Tanox) is an antibody that neutralized C5a by binding to C5a.

C5a activity may also be inhibited by reducing or preventing the formation of C5a. Thus, inhibition of any step in the complement cascade which contributes to the downstream formation of C5a is expected to be effective in practicing the invention. Formation of C5a may be inhibited directly by inhibiting the cleavage of C5 by C5-convertase. Eculizumab (Alexion Pharmaceuticals, Cheshire, Conn.) is an anti-05 antibody that binds to C5 and prevents its cleavage into C5a and C5b. Pexelizumab, an scFv fragment of Eculizumab, has the same activity. Similarly, ARC1905 (Archemix), an anti-05 aptamer, binds to and inhibits cleavage of C5, inhibiting the generation of C5b and C5a.

In another embodiment, formation of C5a is reduced or prevented through the use of a C3 inhibitor. This is a preferred embodiment of the invention, because it also inhibits C3a signaling through the C3a receptor, thereby providing a dual therapeutic effect. Preferably, the C3 inhibitor is compstatin or a compstatin analog, derivative, aptamer or peptidomimetic. Compstatin is a small molecular weight disulfide bonded cyclic peptide having the sequence Ile-Cys-Val-Val-Gln-Asp-Trp-Gly-His-His-Arg-Cys-Thr (SEQ ID NO. 1), Examples of compstatin analogs, derivatives and peptidomimetics are described in the art. See, for instance, U.S. Pat. No. 6,319,897, WO/1999/013899, WO/2004/026328, and Morikis et al (1999, "Design, Structure, Function and Application of Compstatin" in Bioactive Peptides in Drug Discovery and Design: Medical Aspects, Matsoukas et al., eds., IOS Press, Amsterdam NL).

An exemplary compstatin analog comprises a peptide having a sequence: Xaa1-Cys-Val-Xaa2-Gln-Asp-Trp-Gly-Xaa3-His-Arg-Cys-Xaa4 (SEQ ID NO. 2); wherein:

Xaa1 is Ile, Val, Leu, Ac—He, Ac-Val, Ac-Leu or a dipeptide comprising Gly-Ile;

Xaa2 is Trp or a peptidic or non-peptidic analog of Trp;

Xaa3 is His, Ala, Phe or Trp;

Xaa4 is L-Thr, D-Thr, Ile, Val, Gly, or a tripeptide comprising Thr-Ala-Asn, wherein a carboxy terminal —OH of any of the L-Thr, D-Thr, Ile, Val, Gly or Asn optionally is replaced by —NH$_2$; and the two Cys residues are joined by a disulfide bond. Xaa1 may be acetylated, for instance, Ac-Ile. Xaa2 may be a Trp analog comprising a substituted or unsubstituted aromatic ring component. Non-limiting examples include 2-napthylalanine, 1-naphthylalanine, 2-indanylglycine carboxylic acid, dihydrotryptophan or benzoylphenylalanine.

Another exemplary compstatin analog comprises a peptide having a sequence: Xaa1-Cys-Val-Xaa2-Gln-Asp-Xaa3-Gly-Xaa4-His-Arg-Cys-Xaa5 (SEQ ID NO. 3); wherein:

Xaa1 is Ile, Val, Leu, Ac-Tie, Ac-Val, Ac-Leu or a dipeptide comprising Gly-Ile;

Xaa2 is Trp or an analog of Trp, wherein the analog of Trp has increased hydrophobic character as compared with Trp, with the proviso that, if Xaa3 is Trp, Xaa2 is the analog of Trp;

Xaa3 is Trp or an analog of Trp comprising a chemical modification to its indole ring wherein the chemical modification increases the hydrogen bond potential of the indole ring;

Xaa4 is His, Ala, Phe or Trp;

Xaa5 is L-Thr, D-Thr, Ile, Val, Gly, a dipeptide comprising Thr-Asn or Thr-Ala, or a tripeptide comprising Thr-Ala-Asn, wherein a carboxy terminal —OH of any of the L-Thr, D-Thr, Ile, Val, Gly or Asn optionally is replaced by —NH$_2$; and the two Cys residues are joined by a disulfide bond. The analog of Trp of Xaa2 may be a halogenated trpytophan, such as 5-fluoro-1-tryptophan or 6-fluoro-1-tryptophan. The Trp analog at Xaa2 may comprise a lower alkoxy or lower alkyl substituent at the 5 position, e.g., 5-methoxytryptophan or 5-methyltryptophan. In other embodiments, the Trp analog at Xaa 2 comprises a lower alkyl or a lower alkenoyl substituent at the 1 position, with exemplary embodiments comprising 1-methyltryptophan or 1-formyltryptophan. In other embodiments, the analog of Trp of Xaa3 is a halogenated tryptophan such as 5-fluoro-1-tryptophan or 6-fluoro-1-tryptophan.

Other C3 inhibitors include vaccinia virus complement control protein (VCP) and antibodies that specifically bind C3 and prevent its cleavage. Anti-C3 antibodies useful in the present invention can be made by the skilled artisan using methods known in the art. See, for instance, Harlow, et al. (1988, In: Antibodies, A Laboratory Manual, Cold Spring Harbor, N.Y.), Tuszynski et al. (1988, *Blood,* 72:109-115), U.S. patent publication 2003/0224490, Queen et al. (U.S. Pat. No. 6,180,370), Wright et al., (1992, *Critical Rev. in Immunol.* 12(3,4):125-168), Gu et al. (1997, *Thrombosis and Hematocyst* 77(4):755-759) and Burton et al., (1994, *Adv. Immunol.* 57:191-280). Anti-C3 antibodies are also commercially available. Other C3 inhibitors include C3-binding and complement inhibitory secreted *S. aureus* extracellular fibrinogen-binding protein Efb (Lee et al., 2004, *J. Biol. Chem.* 279: 50710-50716) and the Efb homologous protein, Ehp (Hammel et al., 2007, *J. Biol. Chem.* 282: 30051-30061).

In other embodiments, formation of C3a or C5a is reduced or prevented through the use of an inhibitor of complement activation prior C3 cleavage, e.g., in the classical or lectin pathways of complement activation. Non-limiting examples of such inhibitors include, but are not limited to: (1) factor D inhibitors such as diisopropyl fluorophosphates and TNX-234 (Tanox), (2) factor B inhibitors such as the anti-B antibody TA106 (Taligen Therapeutics), (3) C4 inhibitors (e.g., anti-C4 antibodies) and (4) C1q inhibitors (e.g., anti-C1q antibodies). Likewise, inhibitors of signaling via the C3a receptor are also contemplated as being useful in the present invention.

Antibodies useful in the present invention, such as antibodies that specifically bind to either C4, C3 or C5 and prevent cleavage, or antibodies that specifically bind to factor D, factor B, C1q, or the C3a or C5a receptor, can be made by the skilled artisan using methods known in the art. See, for instance, Harlow, et al. (1988, In: Antibodies, A Laboratory Manual, Cold Spring Harbor, N.Y.), Tuszynski et al. (1988, Blood, 72:109-115), U.S. patent publication 2003/0224490, Queen et al. (U.S. Pat. No. 6,180,370), Wright et al., (1992, Critical Rev. in Immunol. 12(3,4):125-168), Gu et al. (1997, Thrombosis and Hematocyst 77(4):755-759) and Burton et al., (1994, Adv. Immunol. 57:191-280). Anti-C3 and anti-05 antibodies are also commercially available.

The invention encompasses the use of pharmaceutical compositions comprising a complement inhibitor to practice the methods of the invention. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

The formulations of the pharmaceutical compositions described herein may be prepared by any method known or hereafter develop in the art of pharmacology. In general, such preparatory methods include the step of bringing the active ingredient into association with a carrier or one or more other accessory ingredients, and then, if necessary or desirable, shaping or packaging the product into a desired single- or multi-does unit.

As used herein, the term "pharmaceutically acceptable carrier" means a chemical composition with which a complement inhibitor may be combined and which, following the combination, can be used to administer the complement inhibitor to a mammal.

As used herein, the term "physiologically acceptable" ester or salt means an ester or salt form of the active ingredient which is compatible with any other ingredients of the pharmaceutical composition, which is not deleterious to the subject to which the composition is to be administered.

The pharmaceutical compositions useful for practicing the invention may be administered to deliver a dose of between 1 ng/kg/day and 100 mg/kg/day. In one embodiment, the invention envisions administration of a dose which results in a concentration of a complement inhibitor between 1 µM and 10 µM. While the precise dosage administered will vary depending upon any number of factors, including but not limited to, the type of patient and type or magnitude of injury being treated, the age of the patient and the route of administration. Preferably, the dosage of the compound will vary from about 1 mg to about 10 g per kilogram of body weight of the patient. More preferably, the dosage will vary from about 10 mg to about 1 g per kilogram of body weight of the patient.

The pharmaceutical composition may be administered to a patient as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease, injury or event being treated, the type and age of the patient, as described above.

In particular embodiments, the pharmaceutical compositions are administered as soon as possible following an ICH event. In other embodiments, additional treatments may be administered at appropriate intervals after the event, e.g., 6, 12 or 24 hours, or periodically for two, three, four or more days after the event, or for one or more weeks after the event.

A single complement inhibitor may be administered or two or more different complement inhibitors may be administered in the practice of the method of the invention. In one embodiment of the invention, the method comprises administration of only a complement inhibitor or a combination of complement inhibitors. In other embodiments, other biologically active agents are administered in addition to the complement inhibitor(s) in the method of the invention. Non-limiting examples of other biologically active agents useful in the invention include antihypertensive drugs to relieve high blood pressure, hyperosmotic agents (mannitol, glycerol, and hypertonic saline solutions) to reduce swelling, and antiinflammatory agents. The administration of complement inhibitors and/or other drugs may also accompany surgical procedures to repair burst blood vessels or other damage associated with the ICH event.

Pharmaceutical compositions that are useful in the methods of the invention may be administered systemically in oral solid formulations, parenteral, intravenous, ophthalmic, suppository, aerosol, topical or other similar formulations. Such pharmaceutical compositions may contain pharmaceutically-acceptable carriers and other ingredients known to enhance and facilitate drug administration. Other formulations, such as nanoparticles, liposomes, resealed erythrocytes, and immunologically based systems may also be used to administer a complement inhibitor according to the methods of the invention.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intravenous, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, in microbubbles for ultrasound-released delivery or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

As used herein, "additional ingredients" include, but are not limited to, one or more of the following: excipients; surface active agents including replacement pulmonary surfactants; dispersing agents; inert diluents; granulating and disintegrating agents; binding agents; lubricating agents;

sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

The following examples are provided to describe the invention in greater detail. They are intended to illustrate, not to limit, the invention.

Example 1

This example describes an investigation of the role of C3a receptor blockade on ICH-induced brain injury using analyses of brain edema formation, leukocyte infiltration, microglial activation as well as neurological outcome following experimental ICH.

Materials and Methods:

Animal Preparation and Intracerebral Infusion. Adult male C57BL/6J mice weighing 23-30 g were used. Mice were randomized to receive intraperitoneal injection of either C3aRA (1 mg/kg) (SB290157, Calbiochem, Darmstadt, Germany) diluted in PBS and DMSO (1.16% v/v), or an equal volume of vehicle (PBS and DMSO, 1.16% DMSO v/v) either 45 minutes prior to ICH induction or 6 and 12 hours after induction of ICH, followed in both cohorts by twice daily doses for 72 hours. The most effective dose of C3aRA (1 mg/kg) was determined in a dose-response trial comparing 0.1 mg/kg, 0.5 mg/kg, 1 mg/kg, 5 mg/kg in a model of focal ischemic stroke. Sham animals were given PBS and DMSO (1.16% v/v) in the same manner.

Mice were anesthetized with a single intraperitoneal dose of ketamine (90 mg/kg) and xylazine (5 mg/kg). Next, the mice were placed in a stereotactic frame (ASI Instruments, Inc., Warren, Mich., USA) and subjected to ICH using autologous blood infusion as previously described (Rynkowski M A et al, 2008, Nat Protoc 3: 122-128), Briefly, a 1-mm burr hole was drilled 2.3 mm lateral to the midline and 0.2 mm anterior to the bregma. Thirty μL of autologous whole blood were drawn from the tail artery into a capillary tube. A 30-gauge needle was then advanced stereotactically through the burr hole into the right striatum (coordinates: 0.2 mm anterior, 2.3 mm lateral to the bregma, 3.5 mm ventral). Using a microinfusion pump (KDS220, KD Scientific Inc., Holliston, Mass., USA), 5 μL was delivered at a rate of 1.5 μL per minute. After a 7-minute period, an additional 25 μL was delivered at a constant rate of 1.5 μL per minute. After a period of 10 minutes, the needle was slowly removed, the burr hole was occluded with bone wax and the skin incision was closed with Nexaband® (Abbott Laboratories, North Chicago, Ill.). Sham animals received only needle insertion. Rectal temperature was maintained at 37.0° C. using a feedback-controlled heating lamp, and the animals recovered in a temperature-controlled incubator for 45 minutes post-procedure.

Neurofunction and behavioral testing. Sensorimotor function was evaluated by means of the 28-point neurological function score, corner test and forelimb placing tests, which were performed pre-operatively and at 6, 24, 48 and 72 hour post-injury. Navigational memory was evaluated with the means of a Morris water-maze (MWM) test pre-operatively and at 72 hours post ICH. Tests were conducted by an observer blinded to the treatment group.

Neurological function. Acute neurological deficits were assessed using a 28-point scoring system including body symmetry, gait, climbing, circling behavior, front limb symmetry, compulsory circling and whisker response. Each point was graded from 0 to 4. The maximum deficit score was 28.

Corner test. For the corner turn test, the mouse was allowed to walk down a corridor into a 30° corner. To exit the corner, the animal could turn either to the right or left. The mouse's choice of turn direction was noted. The number of right and left turns out of 10 total attempts was recorded. The laterality index (LI) and normalized LI were calculated. The laterality index (LI) was calculated for each mouse, according to the formula: LI=(Number of right turns—Number of left turns)/(Total number of turns). The LI for the day before surgery ($LI_{BS}$) and each of the post surgery days was calculated and normalized using the formula:

Normalized $LI=(LI+2)/(LI_{BS}+2)$.

Forelimb placing test. The second behavioral analysis involved a forelimb placing test. The animals were held by their torsos, which allowed the forelimbs to hang free. The animals were moved gently up and down before the placing test to facilitate muscle relaxation. Each forelimb was tested by brushing the respective vibrissae on the corner of a countertop. Intact animals place the forelimb ipsilateral to the stimulated vibrissae quickly onto the countertop. Each animal was tested 10 times for each forelimb, and the percentage of trials in which the mouse placed the appropriate forelimb on the edge of the table after vibrissae stimulation was determined.

Morris water-maze test (MWM). For the MWM test, mice were tested in a pool 80 cm in diameter. The pool was filled with opaque water (deep-white dye added to the water) at a depth of 20 cm. The water temperature was maintained at 26° C. The rescue-landing platform (3 cm in diameter) was submerged by 0.5 cm under the water surface in one of four quadrants. There were navigational cues placed on the walls of the pool and a small flag on the landing platform. Testing consisted of two parts: pre and post-operative. The first part comprised five consecutive training days during which three attempts were given to each mouse to find the platform within 120 seconds. Each mouse was given 20 minutes to rest between swimming trials. The training session occurred at the same time of the day throughout the training and testing periods. A mouse was placed in the water in the quadrant opposite to the landing. The time, in seconds, spent by each animal to find the platform was recorded. If the mouse failed to locate and climb on the platform within the allotted time, it was gently placed and left on the platform for 30 s. On day 4, the flag was removed from the platform and the mouse was given three attempts to locate the platform using only peripheral navigational cues. On day 5, the landing platform was removed and each mouse was placed only one time in the pool for 60 seconds. The time spent in the quadrant where the platform had been situated before was recorded. All the mice that completed the training were operated on the following day. On postoperative day 3, mice were placed in the same swimming pool without the landing platform for 60 seconds. The time spent in the quadrant where the landing had been situated before was recorded in a blinded fashion. Only one attempt was given to each animal.

Histopathology and determination of lesion volume. Following sacrifice, brains were perfused with 4% paraformaldehyde in 0.1 mol/L PBS, pH 7.4, rapidly harvested in one piece, and fixed in 4% paraformaldehyde for 12 hours at 4° C.

Brains were then incubated in 30% sucrose for 2-3 days at 4° C. Next, they were frozen in Optimal Cutting Temperature Compound (O.C.T) Tissue-Tek (#4583, Sakura Finetek USA, Inc., Torrance, Calif., USA) on dry ice then placed at −80° C. Twenty μm coronal sections were cut using a cryostat, and stained using Nissl staining. Striatal lesion volume was determined by digitizing serial coronal sections (50 μm apart) to span the entire hematoma. A blinded observer outlined the region of hematoma (defined by the presence of blood) present in the striatum of the animal. Volume of the lesion ($mm^3$) was then determined by summation of the lesion area in each coronal section and integrating over the section depth of 0.5 mm.

Determination of brain water content. Mice were reanesthetized with Ketamine (80-100 mg/kg i.p.), Xylazine (5-10 mg/kg i.p.) and sacrificed 3 days post-hemorrhage to determine brain water content (sham vehicle n=8 Pre-C3aRA n=8, Post-C3aRA n=11). Brains were removed immediately en bloc and five 2-mm coronal slices were obtained beginning 2-mm from the frontal pole. The brain slices were divided into two hemispheres along the midline. The cortex of each hemisphere was then carefully dissected from the basal ganglia. The cerebellum was retained as a control. Each of the five sections was then weighed on an electronic analytical balance (Model AG 104, Mettler-Toledo, Inc., Columbus, Ohio, USA) to determine the wet weight. The sections were then placed onto pre-weighed cover slips and dried overnight in a vacuum oven for 24 hours to obtain the dry weight. Brain water content (%) was calculated as:

$$((\text{wet weight}-\text{dry weight})/\text{wet weight})\times 100.$$

Preparation of brains. Both cerebral hemispheres were analyzed for inflammatory cells using flow cytometry. Mice were euthanized 72 hours following hemorrhagic stroke onset (sham n=6, vehicle n=7, Pre-C3aRA n=8). Following transcardiac perfusion with phosphate buffered saline (PBS), brains were harvested, divided into ipsilateral and contralateral hemispheres, and minced in RPMI (Invitrogen, Carlsbad, Calif., USA) containing 10% fetal bovine serum (FBS) (Invitrogen; Carlsbad, Calif.). The resulting suspension was passed through a microfilter (70 μm), pelleted, resuspended in 30% Percoll (Amersham, Piscataway, N.J., USA) and centrifuged at 27,000 g for 30 minutes. Following centrifugation, the myelin layer was discarded and the remaining suspension was washed with Dulbecco's phosphate buffered saline containing 1% FBS.

Flow cytometric analysis. Granulocytes were isolated and identified using an antibody-based system. All antibodies used for flow cytometry were rat anti-mouse monoclonal antibodies (BD Pharmingen, Franklin Lakes, N.J., USA): fluorescein isothiocyanate (FITC)-conjugated rat anti-mouse Ly-6G monoclonal antibody, R-phycoerythrin (R-PE)-conjugated rat anti-mouse CD45 monoclonal antibody, and PerCP-Cy5.5-conjugated rat anti-mouse CD11b monoclonal antibody. Antibodies were diluted in D-PBS containing 1% FBS. Cell extracts were incubated simultaneously with the three antibodies and Fc Block (Anti-CD16/CD32) for 30 minutes. Flow cytometric analysis was carried out using a FACSCalibur (BD Biosciences, Franklin Lakes, N.J., USA), and the data were analyzed using FlowJo software (Tree Star, Ashland, Oreg., USA). An antibody to CD45, a cell-surface marker expressed by all leukocytes as well as microglia, was used to exclude all other cell types. The CD11b marker, expressed by all non-lymphocyte leukocytes, was used to distinguish leukocytes from other cell types. Finally, the Ly-6G marker, expressed primarily by granulocytes and lymphocytes, was used to identify granulocytes. Using these three markers, the CD45 positive cells were separated into three general subcategories: (1) Lymphocytes (CD45 positive, CD11b negative, Ly-6G positive) (2) Microglia (CD45 positive, CD11b positive, Ly-6G negative) and (3) Granulocytes (CD45 positive, CD11b positive, Ly-6G positive).

The number of cells that expressed each leukocyte marker was compared to the percentage of the total CD45 positive cells to obtain a percent concentration of each cell subtype. Sham operated animals showed no significant differences in CD45 positive cell populations between hemispheres. There was also no significant difference between the CD45 positive populations between sham hemispheres and hemispheres contralateral to the lesion in the experimental cohorts. Therefore, the non-hemorrhagic (i.e. contralateral) hemisphere was used as a control for each animal and the expression of each marker in the hemorrhagic hemisphere was normalized by comparing it to the expression level present in the non-hemorrhagic hemisphere.

Statistical Analysis. All data are presented as mean±standard error of the mean. Comparisons between groups were made using Kruskal-Wallis ANOVA on ranks or one-way Analysis of Variance (ANOVA) with post-hoc Bonferroni test. A value of $P<0.05$ was considered statistically significant.

Results:

Neurological function and behavioral tests. At six hours after ICH there were marked functional deficits as assessed by the 28-point scoring system, corner turn test and forelimb placing test (FIG. 1). All tests demonstrated a gradual recovery of function in Pre-C3aRA-treated mice (n=24) so that there were no significant deficits compared with sham animals (n=13) at 72 hours after ICH. Compared with Pre-C3aRA-treated animals, vehicle-treated animals (n=24) also showed some recovery of function over time, but they remained significantly inferior to both sham and C3aRA-treated mice in 28-point scale, corner test and forelimb placing test scores at all time points (FIG. 1).

Figure 2:
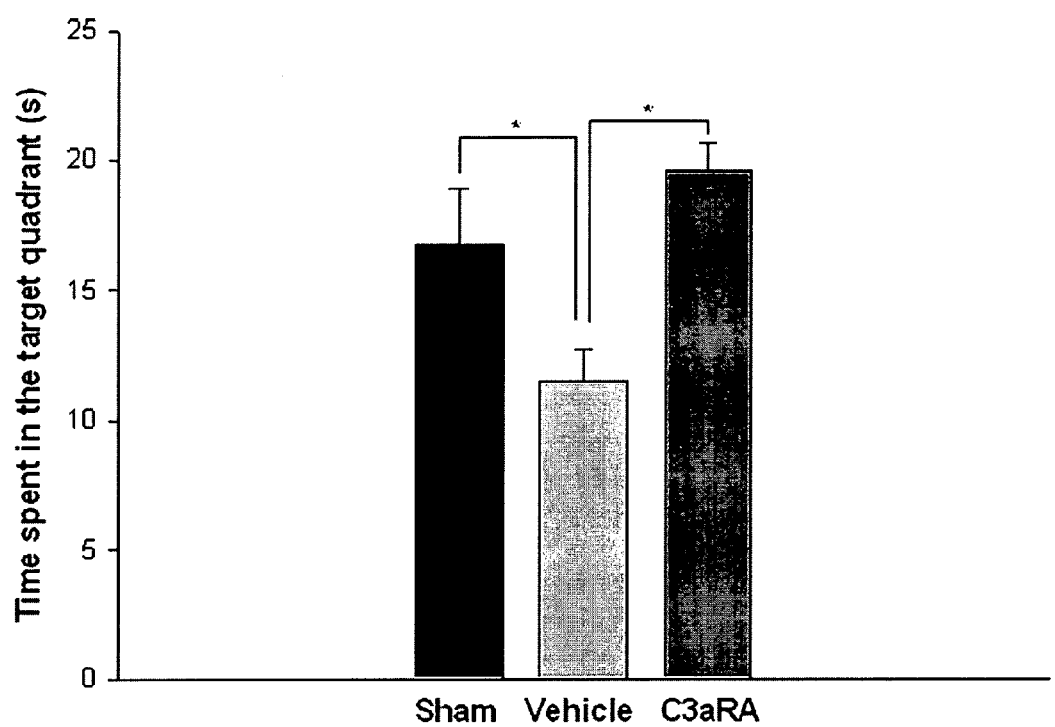
FIG. 2. Morris water-maze performance in sham (n=8), vehicle-treated (n=12) and C3aRA-treated (n=12) mice expressed as the time spent in the target quadrant 72 hours after ICH (16.80±2.08 s vs. 11.52±1.19 s vs. 19.62±1.08 s). Values are expressed as mean±SEM. An * signifies P<0.05.

The MWM test demonstrated a significantly better performance in the Pre-C3aRA-treated mice (n=12) compared with vehicle-treated animals (n=12) at 72 hours after ICH (19.62±1.08 s vs. 11.52±1.19 s, respectively, P<0.05). Additionally, when the C3aRA-treated group was compared with sham animals, there were no statistical differences in the time spent in the target quadrant (19.62±1.08 s vs. 16.80±2.08 s, respectively, P>0.05) (FIG. 2).

Figure 3:
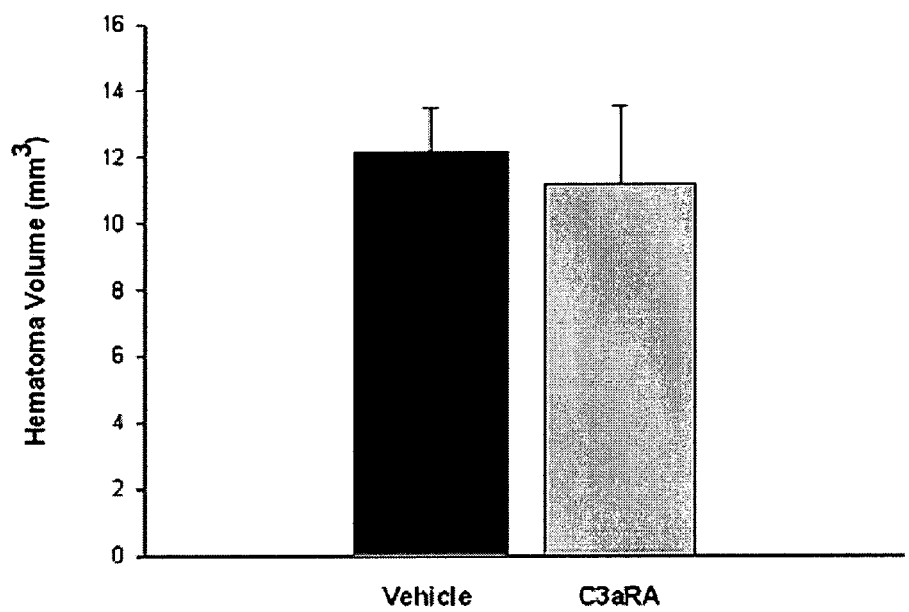
FIG. 3. Mean hematoma volume in vehicle-treated (n=7) and C3aRA-treated (n=7) groups obtained 72 hours after ICH. There was no significant difference in hematoma volume between vehicle and C3aRA-treated mice (11.20±2.35 $mm^3$ vs. 12.17±1.33 $mm^3$ P=0.38). Values are expressed as mean±SEM.

Hematoma Volume. Seventy-two hours after ICH, there was no significant difference in the average hematoma volume between the Pre-C3aRA-treated (n=7) and vehicle-treated (n=7) animals (12.17±1.33 $mm^3$ vs. 11.20±2.35 $mm^3$, respectively, P>0.05) (FIG. 3).

Figure 4:
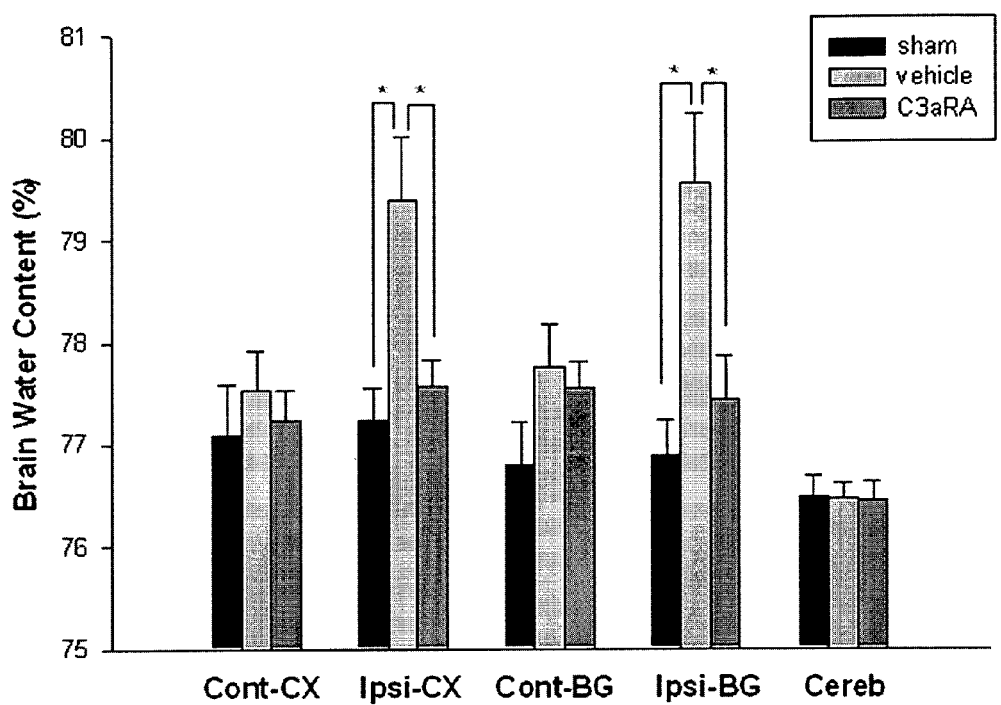
FIG. 4. Brain water content at 72 hours after ICH induction in sham (n=6), vehicle-treated (n=8) and C3aRA-treated (n=8) mice. (ipsilateral cortex: 77.24±031% vs. 79.39±0.61% vs. 77.56±0.26%); (ipsilateral basal ganglia: 76.89±0.34%, vs. 79.54±0.69%, vs. 77.43±0.43%). Values are expressed as mean±SEM. An * signifies P<0.05. Cont-CX, contralateral cortex; Cont-BG, contralateral basal ganglia; Ipsi-CX, ipsilateral cortex; Ipsi-BG, ipsilateral basal ganglia; Cereb, cerebellum.

Brain water content. Three days after ICH, perihematomal brain edema was less in Pre-C3aRA-treated (n=8) than in vehicle-treated mice (n=8) (ipsilateral cortex: 77.56±0.26% vs. 79.39±0.61%, P<0.05; ipsilateral basal ganglia: 77.43±0.43% vs. 79.54±0.69%, P<0.05) (FIG. 4). Water contents in the ipsilateral cortex and in the ipsilateral basal ganglia were not different between Pre-C3aRA-treated and sham mice (ipsilateral cortex: 77.57±0.26% vs. 77.24±0.25%; ipsilateral basal ganglia: 77.43±0.43% vs. 76.89±0.34%) (P>0.05) (FIG. 4), whereas vehicle-treated mice had more brain edema than sham mice (n=6) (ipsilateral cortex: 79.39±0.61% vs. 77.24±0.31%, P<0.05; ipsilateral basal ganglia: 79.54±0.69% vs. 76.89±0.34%, P<0.05). Water content in the contralateral cortex, the basal ganglia and cerebellum was not different in Pre-C3aRA-treated, vehicle-treated and sham animals (FIG. 4). It should be noted that three mice included in the neurological testing did not have tissue results. In two of the mice, tissue was lost from the glass slides during processing and thus had to be excluded. During one of the FACS preparations the pellet was lost during resuspension and the mouse was excluded.

Figure 5:
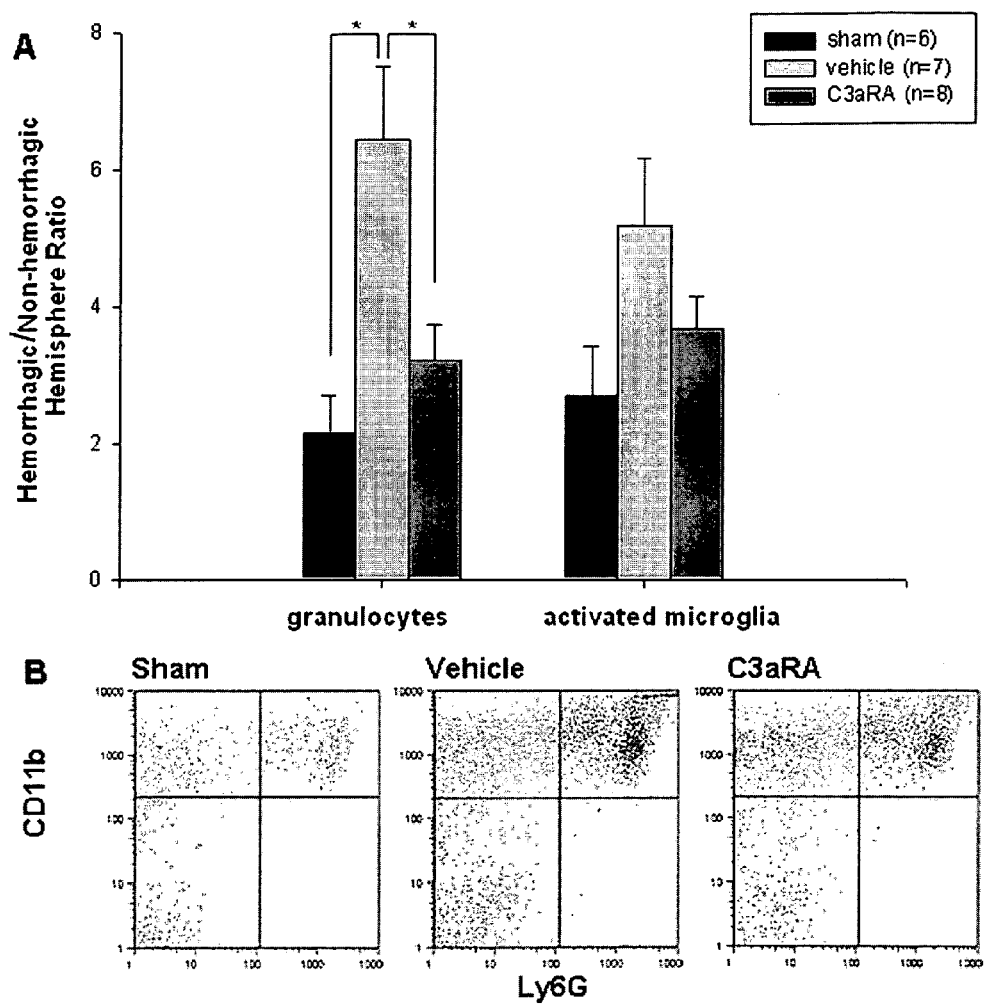
FIG. 5. (A) Hemorrhagic vs. non-hemorrhagic hemisphere ratio of activated microglia and granulocytes in sham (n=6), vehicle (n=7) and C3aRA-treated (n=8) mice at 72 hours after ICH. (Granulocytes: 2.15±0.53 vs. 6.41±1.08 vs. 3.21±0.52); (Microglia: 2.69±031 vs. 5.19±0.97 vs. 3.67±0.45). Values are expressed as mean±SEM. An * signifies P<0.05. (B) FACS plot for all three groups, sorting for CD11b on the Y-axis and Ly6G on the x-axis.

Granulocytes infiltration and microglial activation. Flow cytometric analysis revealed that the granulocyte population, expressed as the hemorrhagic/non-hemorrhagic ratio of cells at 3 days after ICH was less in Pre-C3aRA-treated mice (n=8) than in vehicle-treated mice (n=7) (3.21±0.52 vs. 6.41±1.08, respectively, P<0.05). Additionally, the sham animals (n=6) had a significantly smaller ratio compared with the vehicle-treated group (respectively, 2.15±0.53 vs. 6.41±1.08, P<0.05). There was no difference in hemorrhagic/non-hemorrhagic ratio of granulocyte infiltration between sham and Pre-C3aRA-treated animals (respectively, 2.15±0.53 vs. 3.21±0.52, P>0.05) (FIG. 5). Flow cytometric analysis of microglial activation did not demonstrate any significant differences among the three groups (Pre-C3aRA-treated: 3.67±0.45 vs. vehicle-treated: 5.19±0.97 vs. sham: 2.69±0.71; P=0.087) (FIG. 5).

Figure 6:
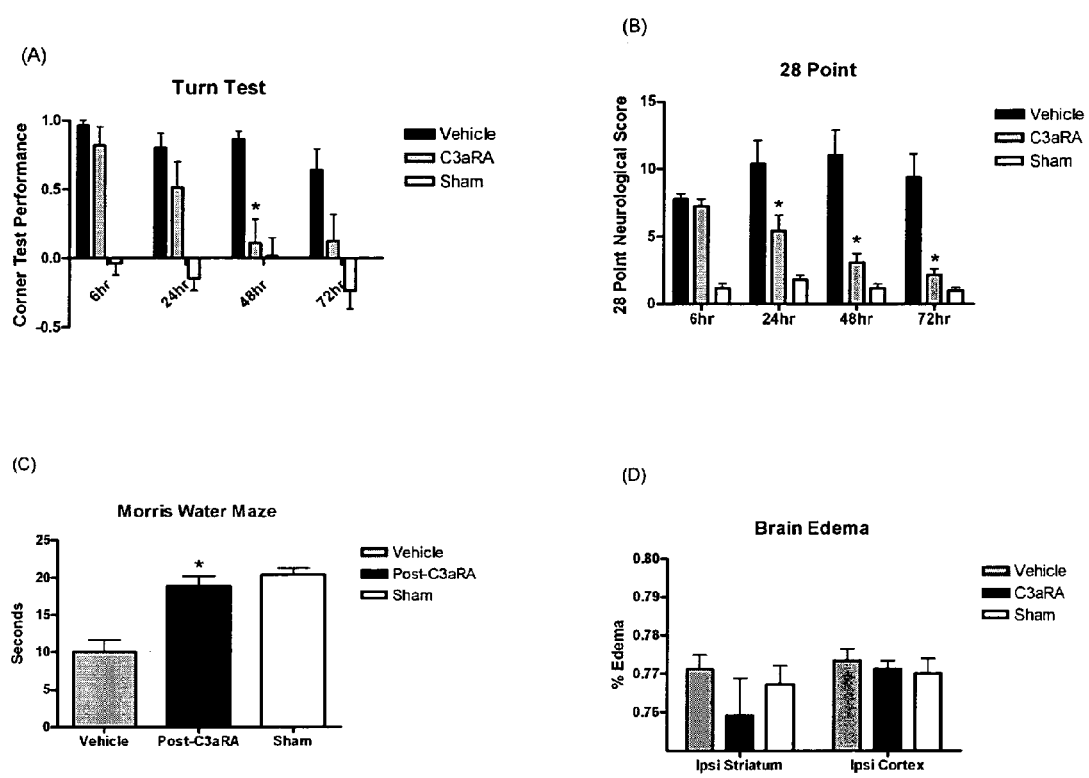
FIG. 6. (A) Corner test performance expressed by the laterality index in vehicle treated (n=17), Post-C3aRA-treated (n=18), and sham (n=11) treated mice at 6, 24, 48, and 72 hours after ICH. First injection given at 6 hours after hemorrhage. (B) 28-point neurological score in vehicle treated (n=16), Post-C3aRA-treated (n=18), and sham mice (n=11) at 6, 24, 48, and 72 hrs after ICH. (C) Morris water-maze performance in vehicle (n=10), Post-C3aRA-treated (n=11), and sham mice (n=11) expressed as the time spent in the target quadrant 72 hours following ICH. Longer times equate to better performance. (D) Brain water content at 72 hours after ICH induction in vehicle treated (n=12), Post-C3aRA-treated (n=11), and sham (n=6) mice. Trend towards decreased edema in C3aRA treated mice. An * signifies a value of P<0.05.

Post-ICH induction dosing of C3aRA. The data above clearly demonstrates that antagonism of the C3aR prior to induction of ICH reduces brain edema and improves neurological outcome. A more clinically relevant model of post-ICH induction dosing of the C3aRA was pursued by dosing first at 6 h, followed by a dose at 12 h and then every 12 hours for 72 hours. Compared with vehicle-treated animals (n=17), post-C3aRA treated mice showed significant improvement at 48 hours in the turn test, and significant improvement at 24, 48, and 72 hours in the 28 point test (FIG. 6). Post-C3aRA-treated mice (n=11) performed significantly better than vehicle-treated animals (n=10) at 72 hours after ICH in the MWM (Post-C3aRA: 18.9±1.3 seconds versus 10±1.7 seconds, p=0.0002. There was no statistical difference between sham animals (n=11) and Post-C3aRA animals in performance in the MWM (sham: 20.4±0.9 seconds, p=NS) (FIG. 6). Post-C3aRA-treated mice (n=11) had mildly decreased brain water content than vehicle (n=12), but this difference did not reach statistical significance (FIG. 6).

Summary:

The results set forth above indicate that C3 is involved in complement-mediated cerebral injury following ICH induction, specifically through the formation of potent pro-inflammatory anaphylatoxin, C3a, and subsequent binding of C3a to the C3a receptor. These data also indicate that the acute inflammatory response to ICH is characterized by granulocyte infiltration and brain edema formation. This complement-mediated neuroinflammatory response is attenuated through C3aRA blockade, leading to marked improvement in neurological function and reduction in brain edema formation. Efficacy with post-ICH administration of C3aR blockade demonstrates the potential of this mechanism of complement blockade to be utilized as a therapeutic in ICH.

Example 2

This example describes further investigation of the role of C3a and C5a in intracerebral hemorrhage. C3a and C5a function was blocked by administering C3a and C5a receptor antagonists both solely and in combination six hours after induced hemorrhage and the outcomes were compared to vehicle-treated controls.

Materials and Methods:

Animal Preparation and Intracerebral Infusion. Adult male C57BL/6J mice weighing 23-30 g were randomized to receive intraperitoneal injection of either C3aRA (1 mg/kg) (SB290157, Calbiochem, Darmstadt, Germany), C5aRA (1 mg/kg), combined C3aRA and C5aRA or an equal volume of DMSO. Each drug was diluted in PBS (1.16% v/v) and given 6 and 12 hours after ICH induction, followed by twice daily doses for 72 hours. The sham group of animals was given PBS and DMSO (1.16% v/v) in the same manner. Mice were anesthetized with a single intraperitoneal dose of ketamine (90 mg/kg) and xylazine (5 mg/kg). Next, the mice were placed in a stereotactic frame (ASI Instruments, Inc., Warren, Mich., USA) and subjected to ICH using autologous blood infusion. Briefly a 1-mm burr hole was drilled 2.3 mm lateral to the midline and 0.2 mm anterior to the bregma. Thirty μL of autologous whole blood was drawn from the tail artery into a capillary tube. A 30-gauge needle was then advanced stereotactically through the burr hole into the right striatum (coordinates: 0.2 mm anterior, 2.3 mm lateral to the bregma, 3.5 mm ventral). A total of 30 μL of autologous whole blood was injected via the double injection technique using a microinfusion pump (KDS220, KD Scientific Inc., Holliston, Mass., USA). An initial amount of 5 μL was delivered at a rate of 1.5 μL per minute. Following a 7 minute period, an additional 25 μL was delivered at a constant rate of 1.5 μL per minute. After a period of 10 minutes, the needle was slowly removed, the burr hole was occluded with bone wax and the skin incision was closed with Nexaband® (Abbott Laboratories, North Chicago, Ill.). Sham animals received only needle insertion. Rectal temperature was maintained at 37.0° C. using a feedback-controlled heating lamp, and the animals recovered in a temperature-controlled incubator for 45 minutes post-procedure.

Neurofunction and behavioral testing. Acute neurological deficits were assessed using a 28-point and corner turn test at 6, 12, 24, 48 and 72 hours post-injury (vehicle n=17, C3aRA n=18, C5aRA n=13, C3aRA/C5aRA n=16 sham n=11). The 28-point scale measures body symmetry, gait, climbing, circling behavior, front limb symmetry, compulsory circling, and whisker response. Each point was graded from 0 to 4. The maximum deficit score was 28. For the corner turn test, the mouse was allowed to walk down a corridor into a 30° corner. To exit the corner, the animal could turn either to the right or left. The mouse's choice of turn direction was noted. The number of right and left turns out of 10 total attempts was recorded. The laterality index (LI) was calculated for each mouse, according to the formula: LI=(Number of right turns−Number of left turns)/(Total number of turns).

Morris water-maze test (MWM). Navigational memory was evaluated by means of a Morris water-maze (MWM) (vehicle n=10 C3aRA n=11 C5aRA n=8 Sham n=11). Testing consisted of five days of pre-operative training followed by one testing period 72 hours post ICH. For the first three days, mice were placed in a 80 cm pool filled with opaque water and given three attempts to find the partially submerged platform within 120 seconds. On day 4, the flag was removed from the platform and the mouse was given three attempts to locate the platform using only peripheral navigational cues. On day 5, the landing platform was removed and each mouse was placed only one time in the pool for 60 seconds. On postoperative day 3, mice were placed in the same swimming pool without the landing platform for 60 seconds. The time spent in the quadrant where the landing had been situated before was recorded in a blinded fashion. Only one attempt was given to each animal.

Determination of brain water content. Mice were reanesthetized with Ketamine (80-100 mg/kg i.p.), Xylazine (5-10 mg/kg i.p.) and sacrificed 3 days post-hemorrhage to determine brain water content (vehicle n=12, C3aRA n=11, C5aRA n=8, C3aRA/C5aRA n=10, and sham n=8). Brains were removed immediately en bloc and divided into two hemispheres along the midline. The cortex of each hemisphere was then carefully dissected from the striatum. The cerebellum was separated and retained as a control. Each of the components was then weighed on an electronic analytical balance (Model AG 104, Mettler-Toledo, Inc., Columbus, Ohio, USA) to determine the wet weight. The sections were then placed onto pre-weighed cover slips and dried overnight in a vacuum oven for 24 hours to obtain the dry weight. Brain water content (%) was calculated as: ((wet weight-dry weight)/wet weight)×100.

Preparation of Brains. Both Cerebral Hemispheres were Analyzed for Infiltrating inflammatory cells using flow cytometry. Mice were euthanized 72 hours following hemorrhagic stroke onset (vehicle n=7, C3aRA n=8, C5aRA n=8, C3aRA/C5aRA n=8, and sham n=7). Following transcardiac perfusion with phosphate buffered saline (PBS), brains were harvested, divided into ipsilateral and contralateral hemispheres, and minced in RPMI (Invitrogen, Carlsbad, Calif., USA) containing 10% fetal bovine serum (FBS) (Invitrogen; Carlsbad, Calif.). The resulting suspension was passed through a microfilter (70 μm), pelleted, resuspended in 30% Percoll (Amersham, Piscataway, N.J., USA) and centrifuged at 27,000 g for 30 minutes. Following centrifugation, the myelin layer was discarded and the remaining suspension was washed with Dulbecco's phosphate buffered saline containing 1% FBS.

Flow cytometric Analysis. Granulocytes were isolated and identified using an antibody-based system. All antibodies used for flow cytometry were rat anti-mouse monoclonal antibodies (BD Pharmingen, Franklin Lakes, N.J., USA): flourescein isothiocyanate (FITC)-conjugated rat anti-mouse Ly-6G monoclonal antibody, R-phycoerythrin (R-PE)-conjugated rat anti-mouse CD45 monoclonal antibody, and PerCP-Cy5.5-conjugated rat anti-mouse CD11b monoclonal antibody. Antibodies were diluted in D-PBS containing 1% FBS. Cell extracts were incubated simultaneously with the three antibodies and Fc Block (Anti-CD16/CD32) for 30 minutes. Flow cytometric analysis was carried out using a FACS Calibur (BD Biosciences, Franklin Lakes, N.J., USA), and the data were analyzed using FlowJo software (Tree Star, Ashland, Oreg., USA). An antibody to CD45, a cell-surface marker expressed by all leukocytes as well as microglia, was used to exclude all other cell types. The CD11b marker, expressed by all non-lymphocyte leukocytes, was used to distinguish leukocytes from other cell types. Finally, the Ly-6G marker, expressed primarily by granulocytes and lymphocytes, was used to identify granulocytes. Using these three markers, the CD45 positive cells were separated into three general subcategories: (1) Lymphocytes (CD45 positive, CD11b negative, Ly-6G positive) (2) Microglia (CD45 positive, CD11b positive, Ly-6G negative) and (3) Granulocytes (CD45 positive, CD11b positive, Ly-6G positive). The number of cells that expressed each leukocyte marker was compared to the number of total CD45 positive cells to obtain a percent concentration of each cell subtype. This percentage was compared to the non-hemorrhagic hemisphere and thus yielded a hemorrhagic/non-hemorrhagic ratio.

Statistical Analysis. All data are presented as mean±standard error of the mean. Comparisons between groups were made using Kruskal-Wallis ANOVA on ranks and compared to control. A value of P<0.05 was considered statistically significant.

Figure 7:
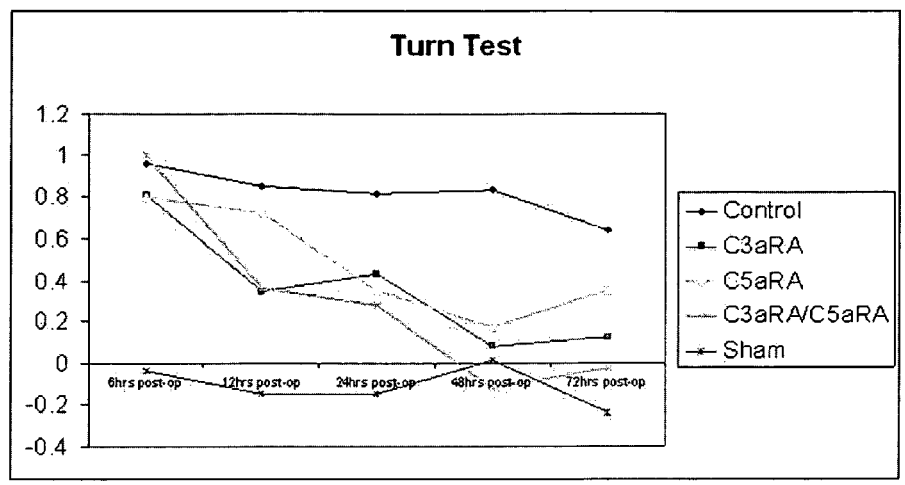
FIG. 7. Corner test performance expressed by the laterality index in vehicle-treated (n=17), C3aRA-treated (n=18), C5aRA-treated (n=13), C3aRA/C5aRA-treated (n=16), and sham (n=11) mice at 6, 12, 24, 48 and 72 hours after intrastriatal infusion of 30 μL autologous blood. First injection was given at 6 hours after hemorrhage. Values are expressed as mean±SEM. *Significantly different compared to vehicle by Kruskal-Wallis ANOVA on ranks (P<0.05).
Figure 8:
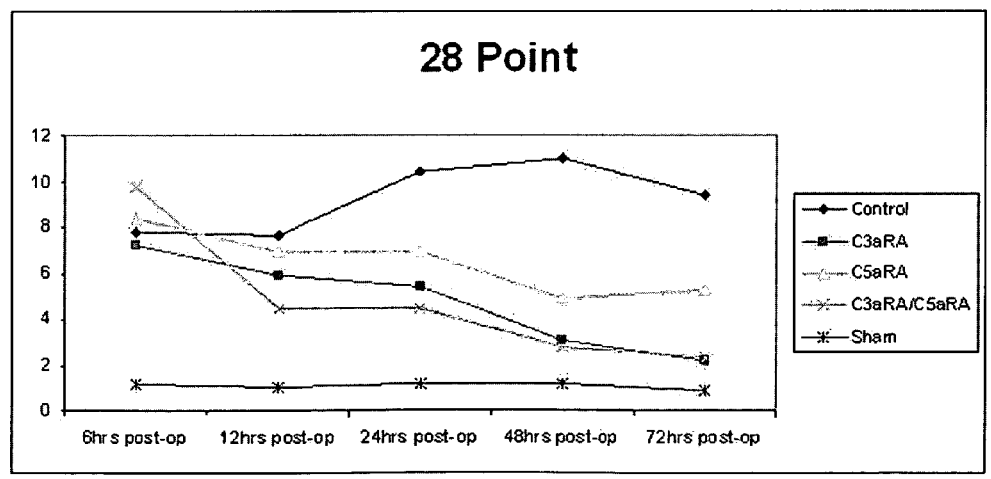
FIG. 8. 28-point neurological score in vehicle-treated (n=17), C3aRA-treated (n=18), C5aRA-treated (n=13), C3aRA/C5aRA-treated (n=16) and sham mice (n=11) at 6, 12, 24, 48 and 72 hours after intrastriatal infusion of 30 μL autologous blood. First injection was given at 6 hours after hemorrhage. Values are expressed as mean±SEM. *Significantly different compared to vehicle by Kruskal-Wallis ANOVA on ranks (P<0.05).

Results:

Neurological function and behavioral tests. At six hours after ICH, when the first drug injection was given, there were significant behavioral deficits in each cohort over sham as assessed using the 28-point scoring system and corner turn test (FIG. 7). All tests demonstrated a gradual recovery of function in C3aRA-treated mice (n=18), C5aRA-treated mice (n=13) C3aRA/C5aRA-treated mice (n=16) over 72 hours after ICH. Compared with vehicle-treated animals (n=17), C3aRA-treated mice, C5aRA-treated mice, and C3aRA/C5aRA-treated mice showed significant improvement at 48 hours in the turn test (FIG. 7) and significant improvement at 24, 48 and 72 hours in the 28 point test FIG. 8).

Figure 9:
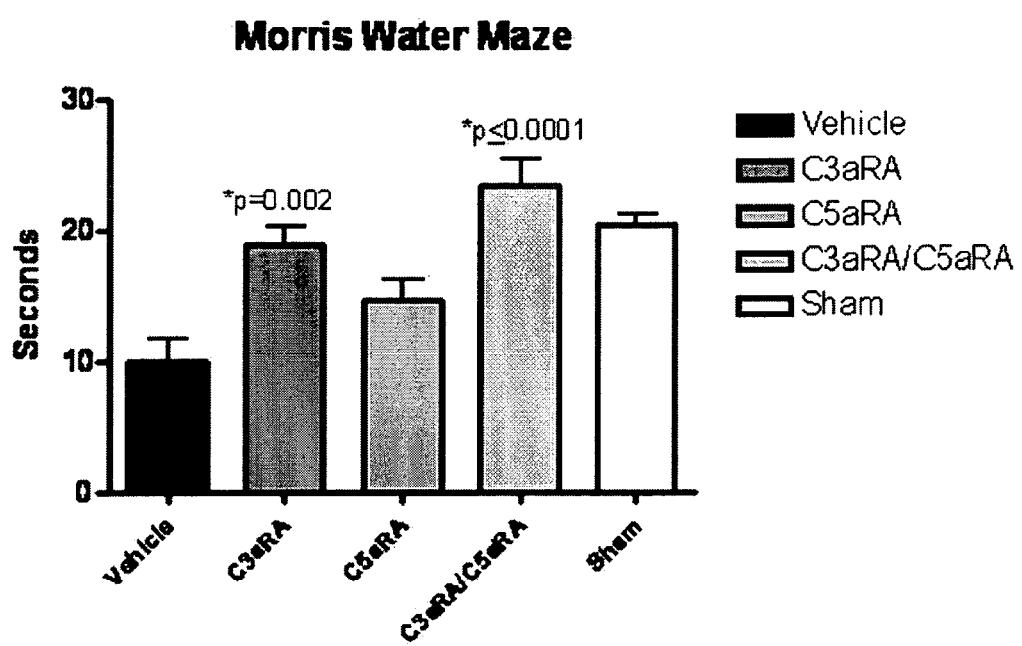
FIG. 9. Morris water-maze performance in vehicle-treated (n=10), C3aRA-treated (n=11), C5aRA-treated (n=8), C3aRA/C5aRA-treated (n=9), and sham mice (n=11) expressed as the time spent in the target quadrant 72 hours after ICH. Values are expressed as mean±SEM. *Significantly different from vehicle by Kruskal-Wallis ANOVA on ranks (P<0.05).

Morris water-maze test (MWM). The MWM test demonstrated a significantly better performance in C3aRA-treated mice (n=11) and C3aRA/C5aRA (n=9) compared with vehicle-treated animals (n=10) at 72 hours after ICH(C3aRA: 18.9±1.3 seconds p=0.002 C3aRA/C5aRA: 23.4±2.0 seconds p<0.0001 vs. Vehicle: 10.0±1.7 seconds). Additionally, when the C3aRA-treated and C3aRA/C5aRA-treated groups were compared with sham animals (n=11), there were no statistical differences in the time spent in the target quadrant (sham: 20.4±0.9 seconds p=ns). (FIG. 9).

Figure 10A:
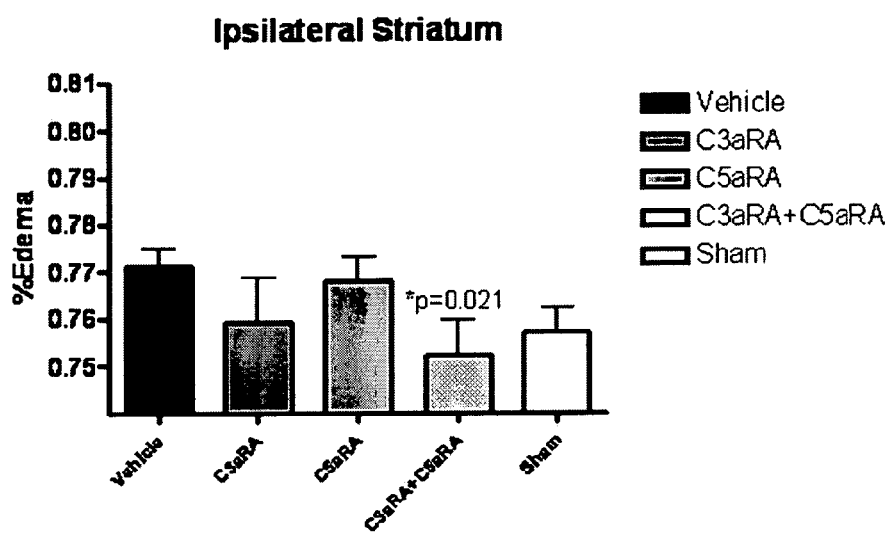
FIG. 10. Brain water content in the striatum (FIG. 10A) and cortex (FIG. 10B) at 72 hours after ICH induction in vehicle-treated (n=12), C3aRA-treated (n=11), C5aRA-treated (n=8), C3aRA/C5aRA-treated mice (n=10) and sham (n=6) mice. * Significantly different from vehicle by Kruskal-Wallis ANOVA on ranks (P<0.05).
Figure 10B:
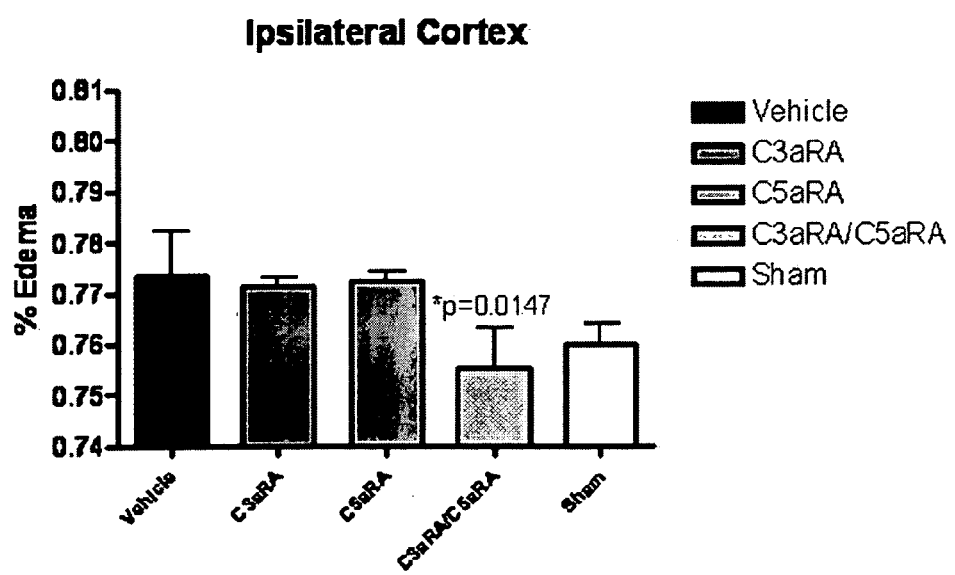
Figure 11:
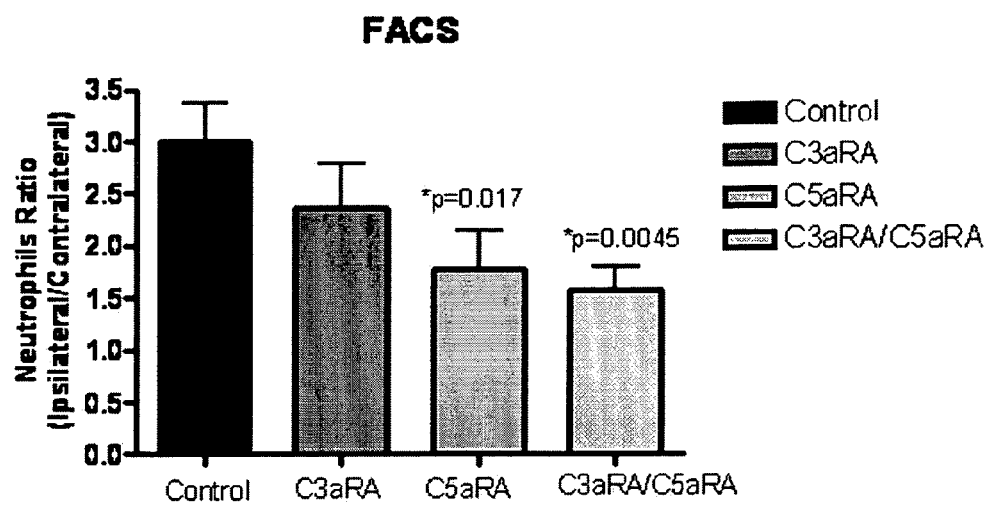
FIG. 11. Hemorrhagic vs. non-hemorrhagic hemisphere ratio of activated granulocytes in vehicle-treated (n=7), C3aRA-treated (n=8), C5aRA-treated (n=8), C3aRA/C5aRA-treated (n=8) and sham (n=7) mice at 72 hours after ICH. Values are expressed as mean±SEM. *Significantly different from vehicle by Kruskal-Wallis ANOVA on ranks (P<0.05).

Brain water content. C3aRA-treated (n=11) and C5aRA-treated (n=8) mice had mildly decreased brain water content over control but only C3aRA/C5aRa-treated (n=10) mice reached statistical significance over vehicle-treated mice (n=12) (ipsilateral cortex: C3aRA/C5aRA: 0.755403±0.008 versus 0.773327±0.003 p=0.02 ipsilateral striatum: 0.752273±0.007 versus 0.771163±0.0036 p=0.007) (FIG. 10).

Water contents in the ipsilateral cortex and in the ipsilateral basal ganglia were not different in C3aRA/C5aRA-treated and sham mice (n=6) (Sham: ipsilateral cortex: 0.770026±0.004 ipsilateral striatum: 0.76717±0.005 p=ns). Water content in the contralateral cortex, contralateral striatum, and cerebellum was not statistically different in any of the groups (data not shown).

Granulocytes infiltration and activation. Flow cytometric analysis revealed that granulocyte infiltration, expressed as the hemorrhagic/non-hemorrhagic ratio of cell infiltration at 3 days after ICH was less in C5aRA-treated (n=8) and C3aRA/C5aRA-treated mice (n=8) than in vehicle-treated mice (n=7) (C5aRA: 1.7793±0.36 p=0.017 C3aRA/C5aRA: 1.58534±0.2164 p=0.0045 versus vehicle: 3.010886±0.35747). Sham operated animals (n=7) showed no significant differences in CD45 positive cell populations between hemispheres.

Summary:

The results set forth in this example indicate that both C3 and C5 are involved in complement-mediated cerebral injury following ICH induction. Without being bound by any explanation of mechanism, it is believed that the formation of the potent pro-inflammatory anaphylatoxins C3a and C5a and subsequent binding to their respective receptors leads to increased leukocyte infiltration and brain edema formation. It is demonstrated herein that these outcomes can be attenuated through selective blockade, leading to marked improvement in neurological function.

The present invention is not limited to the embodiments described and exemplified above, but is capable of variation and modification within the scope of the appended claims.

What is claimed is:

1. A method for treating or reducing injury resulting from intracerebral hemorrhage in an individual, the method comprising administering a therapeutically effective amount of at least one complement inhibitor to the individual, wherein the at least one complement inhibitor reduces or prevents C3a and C5a formation or activity, thereby treating or preventing the injury resulting from intracerebral hemorrhage, and wherein the at least one complement inhibitor comprises:
   (a) a C3 inhibitor, a C4 inhibitor, or a combination thereof; or
   (b) a C3 inhibitor, a C3aR inhibitor, or a C4 inhibitor in combination with:
      (i) a C5a inhibitor;
      (ii) a C5aR inhibitor; or
      (iii) a C5a inhibitor and a C5aR inhibitor.

2. The method of claim 1, wherein the at least one complement inhibitor is a C3 inhibitor, a C3aR inhibitor, or a C4 inhibitor in combination with a C5a inhibitor or a C5aR inhibitor.

3. The method of claim 2, wherein the C5a inhibitor or C5aR inhibitor is acetyl-Phe-[Orn-Pro-D-cyclohexylalanine-Trp-Arg] (PMX-53), PMX-53 analogs, neutrazumab, TNX-558, eculizumab, pexelizumab or ARC1905, or any combination thereof.

4. The method of claim 1, wherein the at least one complement inhibitor is a C3 inhibitor.

5. The method of claim 4, wherein the C3 inhibitor is compstatin, a compstatin analog, a compstatin peptidomimetic, a compstatin derivative, or any combinations thereof.

6. The method of claim 5, wherein the C3 inhibitor comprises:
   (a) Ile-Cys-Val-Val-Gln-Asp-Trp-Gly-His-His-Arg-Cys-Thr (SEQ ID NO. 1); or
   (b) Xaa1-Cys-Val-Xaa2-Gln-Asp-Trp-Gly-Xaa3-His-Arg-Cys-Xaa4 (SEQ ID NO. 2); wherein Xaa1 is Ile, Val, Leu, Ac-Ile, Ac-Val, Ac-Leu or a dipeptide comprising Gly-Ile; Xaa2 is Trp or a peptidic or non-peptidic analog of Trp; Xaa3 is His, Ala, Phe or Trp; Xaa4 is L-Thr, D-Thr, Ile, Val, Gly, or a tripeptide comprising Thr-Ala-Asn, wherein a carboxy terminal —OH of any of the L-Thr, D-Thr, Ile, Val, Gly or Asn optionally is replaced by —NH$_2$; and the two Cys residues are joined by a disulfide bond; or
   (c) Xaa1-Cys-Val-Xaa2-Gln-Asp-Xaa3-Gly-Xaa4-His-Arg-Cys-Xaa5 (SEQ ID NO. 3); wherein Xaa1 is Ile, Val, Leu, Ac-Ile, Ac-Val, Ac-Leu or a dipeptide comprising Gly-Ile; Xaa2 is Trp or an analog of Trp, wherein the analog of Trp has increased hydrophobic character as compared with Trp, with the proviso that, if Xaa3 is Trp, Xaa2 is the analog of Trp; Xaa3 is Trp or an analog of Trp comprising a chemical modification to its indole ring wherein the chemical modification increases the hydrogen bond potential of the indole ring; Xaa4 is His, Ala, Phe or Trp; and Xaa5 is L-Thr, D-Thr, Ile, Val, Gly, a dipeptide comprising Thr-Asn or Thr-Ala, or a tripeptide comprising Thr-Ala-Asn, wherein a carboxy terminal —OH of any of the L-Thr, D-Thr, Ile, Val, Gly or Asn optionally is replaced by —NH$_2$; and the two Cys residues are joined by a disulfide bond.

7. The method of claim 1, wherein the at least one complement inhibitor is a C4 inhibitor.

8. The method of claim 1, wherein the at least one complement inhibitor is administered or targeted to affected tissue.

9. The method of claim 1, wherein the at least one complement inhibitor is administered systemically.

10. The method of claim 1, wherein the at least one complement inhibitor is administered together or concurrently with, or sequentially before or after, at least one other agent for treatment of injury resulting from intracerebral hemorrhage.

* * * * *